(12) United States Patent
Ogawa et al.

(10) Patent No.: US 7,767,413 B2
(45) Date of Patent: Aug. 3, 2010

(54) REAGENT, MEDIUM, AND METHOD FOR DETECTION OF ALICYCLOBACILUS ACIDOTERRESTRIS

(75) Inventors: Hiroyuki Ogawa, Sendai (JP); Mitsuyoshi Miyashita, Sendai (JP)

(73) Assignee: MicroBio Kabushiki Kaisha, Sendai-shi (JP)

( * ) Notice: Subject to any disclaimer, the term of this patent is extended or adjusted under 35 U.S.C. 154(b) by 208 days.

(21) Appl. No.: 11/918,140

(22) PCT Filed: Apr. 18, 2006

(86) PCT No.: PCT/JP2006/308153
§ 371 (c)(1),
(2), (4) Date: Oct. 10, 2007

(87) PCT Pub. No.: WO2006/112461
PCT Pub. Date: Oct. 26, 2006

(65) Prior Publication Data
US 2009/0023179 A1    Jan. 22, 2009

(30) Foreign Application Priority Data
Apr. 18, 2005    (JP) .............................. 2005-120210

(51) Int. Cl.
G01N 33/53    (2006.01)
G01N 33/569    (2006.01)
(52) U.S. Cl. .......................... 435/34; 435/7.32; 435/7.1
(58) Field of Classification Search ........................ None
See application file for complete search history.

(56) References Cited
FOREIGN PATENT DOCUMENTS

| | | |
|---|---|---|
| JP | 6-078793 | 3/1994 |
| JP | 2004-041104 | 2/2004 |

OTHER PUBLICATIONS

Sandstedt et al. Thermotolerant Campylobacter With No Or Weak Catalase Activity Isolated From Dogs; Current Microbiology, vol. 8 (1983) pp. 209-213.*
Beloti et al. Frequency of 2,3,5-Triphenyltetrazolium Chloride (TTC) Non-Reducing Bacteria in Pastuerized Milk; Revista de Microbiologica, vol. 30 (1999) pp. 137-140.*
Tengerdy et al. Quantitative Measurement of Bacterial Growth by the Reduction of Tetrazolium Salts; Applied Microbiology, vol. 15, No. 4 (1967) pp. 954-955.*
Jimenez-Valera et al. Comparison of Ceftriaxone, Amikacin, and Ciprofloxacin in Treatment of Experimental Yersinia Enterocolitica 09 Infection in Mice; Antimicrobial Agents and Chemotherapy, vol. 42, No. 11 (1998) pp. 3009-3011.*
Kitamura, Kazuhisa et al., "Teishoku Hannoshiki ni yoru Ekitai Baichi o Mochiita Alicyclobacillus-Zoku Saikin no Jinsoku Kenshutsu Hoho", *Nippon Nogei Kagaku Kaishi*, 2001, p. 267, 3M1p3, vol. 75.

* cited by examiner

*Primary Examiner*—Rebecca E. Prouty
*Assistant Examiner*—Paul C. Martin
(74) *Attorney, Agent, or Firm*—Oliff & Berridge, PLC

(57) ABSTRACT

To supply the reagent, medium, and method for detection of *Alicyclobacilus acidoterrestris*, with which *acidoterrestris* can be rapidly detected and easily distinguished from *acidocaldarius*.

After a sample including fruit juice is added to the medium for detection of *Alicyclobacilus acidoterrestris* containing chlor-2,3,5-triphenyl-2H-tetrazolium, *acidoterrestris* bacteria are detected based upon color change to red of the colony on the medium, which is kept at the temperature of 40 to 50° C.

5 Claims, 4 Drawing Sheets
(4 of 4 Drawing Sheet(s) Filed in Color)

REAGENT, MEDIUM, AND METHOD FOR DETECTION OF ALICYCLOBACILUS ACIDOTERRESTRIS

BACKGROUND OF THE INVENTION

1. Field of the Invention

This invention relates the reagent, medium, and method for detection of *Alicyclobacilus acidoterrestris*.

2. Description of the Related Art

A wide range of *Alicyclobacilus* bacteria such as *Alicyclobacilus acidocaldarius* (hereinafter "*acidocaldarius*") and *Alicyclobacilus acidoterrestris* (hereinafter "*acidoterrestris*") exist in soil. *Alicyclobacilus* bacteria are gram-positive bacillus that form thermophil and acidophil spore, and not killed by usual Pasteur sterilization. Among *Alicyclobacilus* bacteria, *acidoterrestris* generate components emitting a foul odor; therefore, it is important to detect the bacteria contamination because it becomes to be a cause of putrefaction.

So far, there is a test method to detect the contamination of *acidoterrestris*, by which growth of the colony is compared by observing with naked eyes after cultivation for 14-24 hours simultaneously at 2 temperatures of 40-50° C. and 60-70° C. (refer to Japanese Patent Laid-Open No. 2004-41104).

However, because range of temperature at which *acidoterrestris* can grow is from around 25° C. to 50° C. and that at which *acidocaldarius* can grow is from 40° C. to 65° C., the above test has had a problem that it is difficult to distinguish the grown colonies between those of *acidocaldarius* and those of *acidoterrestris*.

Therefore, *acidoterrestris* has been selectively detected by setting the temperature of the culture at around 30° C. so that the growth of *acidocaldarius* can be inhibited.

However, in the previous test method there has been still another problem that it takes more than 48 hours to detect *acidoterrestris* because the growth of *acidoterrestris* is delayed at the temperature around 30° C. although the optimum temperature for the growth of *acidoterrestris* is around 45° C. Besides, the colonies of grown *acidoterrestris* on the medium are white and it is another problem that it is difficult to observe the colonies on the semi-transparent medium.

The present invention has focused on such problems and aims to detect *acidoterrestris* rapidly and to supply the reagent, medium and method for easy detection of *Alicyclobacilus acidoterrestris* distinguishably from *acidocaldarius*.

SUMMARY OF THE INVENTION

In order to achieve the above aims, the reagent for detection of *Alicyclobacilus acidoterrestris* embraced in the present invention is characterized by consisting of chlor-2,3,5-triphenyl-2H-tetrazolium.

The medium for detection of *Alicyclobacilus acidoterrestris* embraced in the present invention is characterized by containing chlor-2,3,5-triphenyl-2H-tetrazolium.

The method for detection of *Alicyclobacilus acidoterrestris* embraced in the present invention is characterized by detection of the above bacteria based upon color change of the colony on the above medium, which is kept under the conditions of culture of *Alicyclobacilus acidoterrestris* after a sample is added to the medium for detection of *Alicyclobacilus acidoterrestris* containing chlor-2,3,5-triphenyl-2H-tetrazolium.

As the method for detection of *Alicyclobacilus acidoterrestris* embraced in the present invention, detection of the above bacteria based upon becoming red of the colony on the above medium, which is kept at 40 to 50° C. after applying the sample containing fruit juice to surface of the medium for detection of *Alicyclobacilus acidoterrestris* containing chlor-2,3,5-triphenyl-2H-tetrazolium, is preferable.

Chlor-2,3,5-triphenyl-2H-tetrazolium (Triphenyl Tetrazoium Chloride, hereinafter "TTC") is colorless in the oxidative state, but when it is incorporated into the growing bacteria and reduced, it becomes red and insoluble formazan. Reduction of TTC is irreversible and once produced formazan is neither re-oxidized in air nor changed to white.

By addition of TTC to the medium *acidoterrestris* is changed to red and detection of the bacteria becomes easy. On the other hand, *acidocaldarius* is not changed by addition of TTC to the medium. Thus, *acidoterrestris* is easily distinguished from *acidocaldarius*.

TTC is known to become red with gram-negative bacteria, and can make the detection of such bacteria easy. Also, TTC is hardly changed in its color with lactic acid bacteria and gram-positive bacteria. However, it has not been reported that TTC is changed to red or not with different species among the same genus of bacteria. Thus, it has not been known that TTC is changed to red with *acidoterrestris* but not with *acidocaldarius*.

The present invention is done based upon the observation.

TTC is preferably contained in the medium in the range of 20 mg/L and 50 mg/L, especially, in the range of 20 mg/L and 40 mg/L, furthermore, more preferable in the range around 30 mg/L. Because it is hard to detect the color change when concentration of TTC is less than 20 mg/L, whereas, TTC is effective on the growth of *acidoterrestris* when its concentration is higher than 40 mg/L, and the effect becomes large when its concentration is over 50 mg/L.

As the medium, YSG medium containing yeast extract, starch, and glucose as main components is preferable, and its pH is preferably adjusted to 3.7±0.2. Sulfuric acid is preferable as the pH adjuster. Citric acid and lactic acid can be used to adjust the pH but not preferable, because they are effective on the growth of *acidoterrestris*. Liquid medium can also be used but agar medium is preferable. When agar medium is used as the medium, the sample is preferably added to the medium by applying to the surface, but not preferable by application of the mix-dilution method because its color changes are hardly occurred by the mix-dilution method. As the sample, any samples expected the detection of *acidoterrestris* can be used but fruit juices such as orange juice, drinking cooling beverages, wine, and fruit cans such as orange can are suitable.

As the conditions of *acidoterrestris* culture, temperature is preferably kept at 40° C. to 50° C., especially 42° C. to 45° C. and pH is preferably adjusted to 3.7±0.2 in acidic field.

It is possible to detect *acidoterrestris* within 24 hours with naked eyes by keeping the optimum conditions of *acidoterrestris* culture in the medium including TTC. When a detecting device is used it is possible to detect the bacteria within 15 hours. Although addition of TTC to the medium has little effect on the growth rate of *acidoterrestris*, the growth rate of *acidocaldarius* is affected by addition of TTC and becomes late. Thus, the bacteria can be detected for about 35 hours on the medium without TTC but the time to detect the bacteria is delayed longer than 45 hours. Therefore, the medium in the presence of TTC has advantages that *acidoterrestris* can be easily distinguished from *acidocaldarius* by color change to red and that the growth of *acidocaldarius* is inhibited to distinguish from that of *acidoterrestris*.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE PREFERRED EMBODIMENT

Hereinafter, the embodiment of the present invention is explained according to the drawings.

YSG agar medium including TTC was prepared as follows. To 1 L of water, 2 g of yeast extract, 1 g of glucose, 15 g of dried agar, and 30 g of chlor-2,3,5-triphenyl-2H-tetrazolium (TTC) were added, and pH of the mixture was adjusted to 3.7 with 1 N sulfuric acid. The mixture was sterilized and poured into dishes. After the sample was applied to the surface of the prepared medium for detection of *Alicyclobacilus acidoterrestris*, it was cultured for 48 hours keeping the temperature at 45° C. Samples were (a) water including *acidoterrestris* and (b) water including *acidocaldarius*. As the blank, YSG agar medium was prepared in the same manner except for without addition of TTC and the same samples were cultured for 48 hours.

The results are shown in FIGS. 1 to 4.

Figure 1:
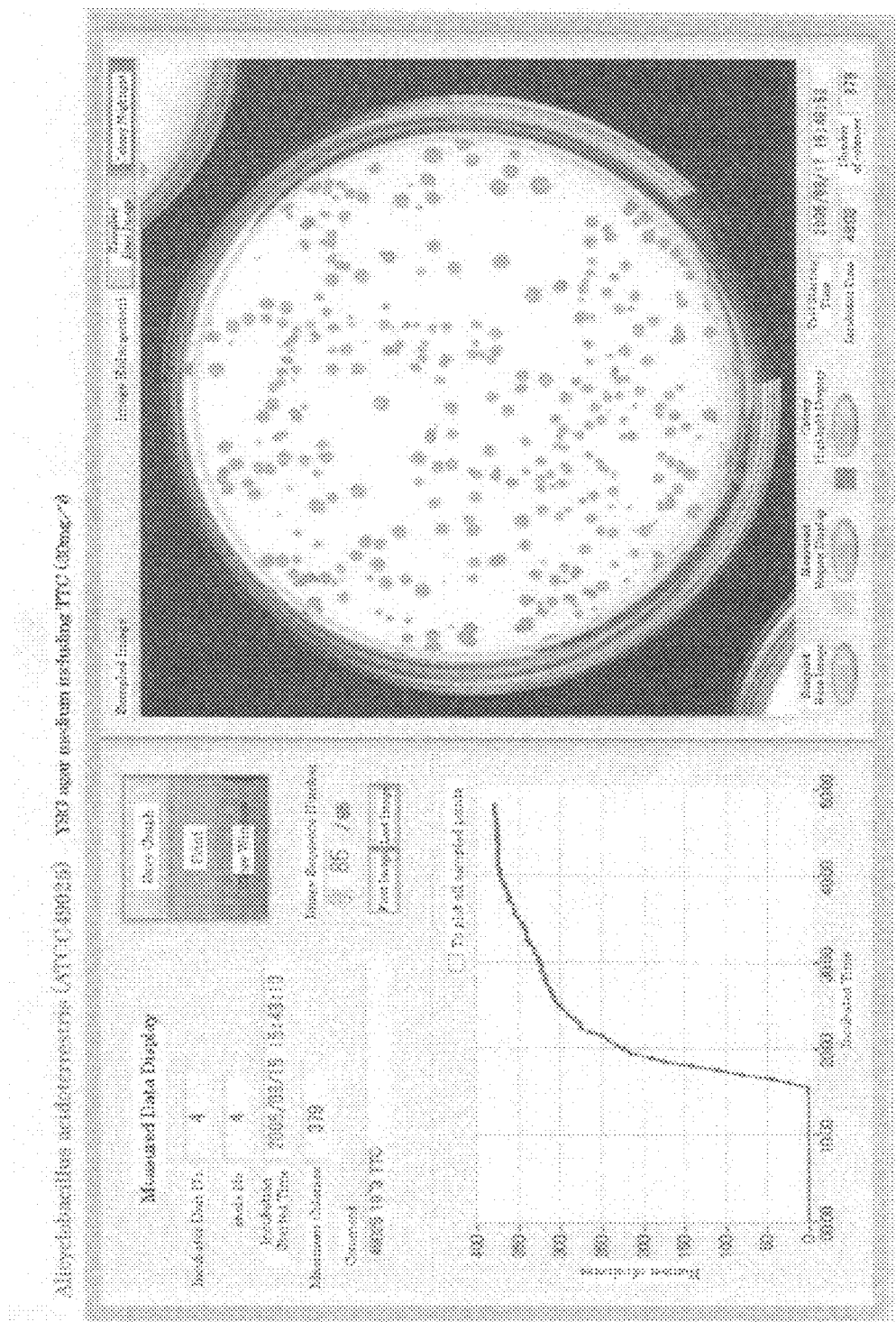
FIG. 1 is a drawing in embodiment representing a graph showing changes in number of colonies depending the culture time when (a) water including *acidoterrestris* is applied to the surface of YSG agar medium including TTC, and a photograph showing colonies on the medium at 48 hours culture.

FIG. 1 represents a graph showing changes in number of colonies depending the culture time when (a) water including *acidoterrestris* is applied to the surface of YSG agar medium including TTC, and a photograph showing colonies on the medium at 48 hours culture. Colonies are shown in red.

Figure 2:
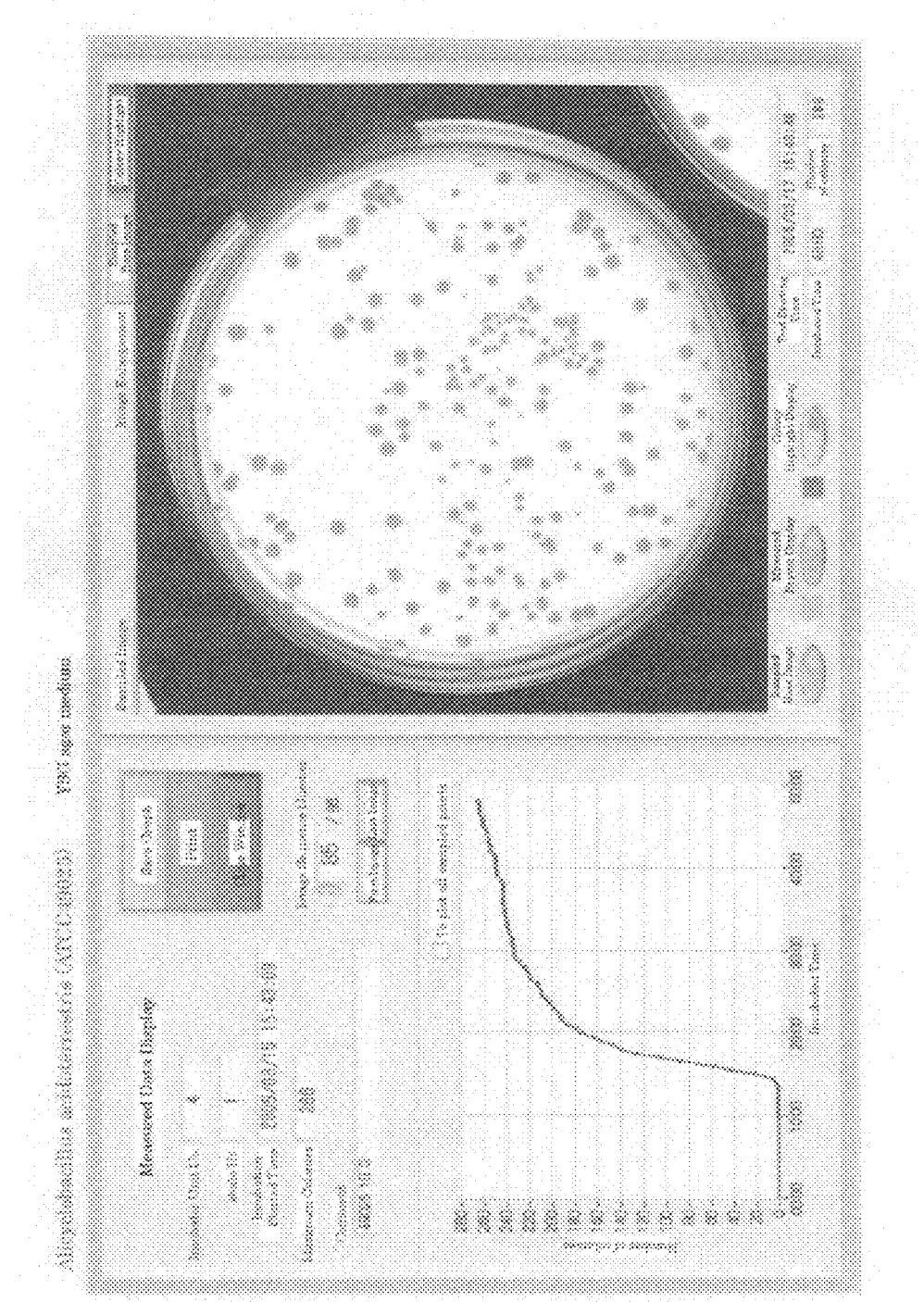
FIG. 2 is a drawing in embodiment representing a graph showing changes in number of colonies depending the culture time when (a) water including *acidoterrestris* is applied to the surface of blank YSG agar medium without TTC, and a photograph showing colonies on the medium at 48 hours culture.

FIG. 2 represents a graph showing changes in number of colonies depending the culture time when (a) water including *acidoterrestris* is applied to the surface of blank YSG agar medium without TTC, and a photograph showing colonies on the medium at 48 hours culture. Colonies are shown in green.

Figure 3:
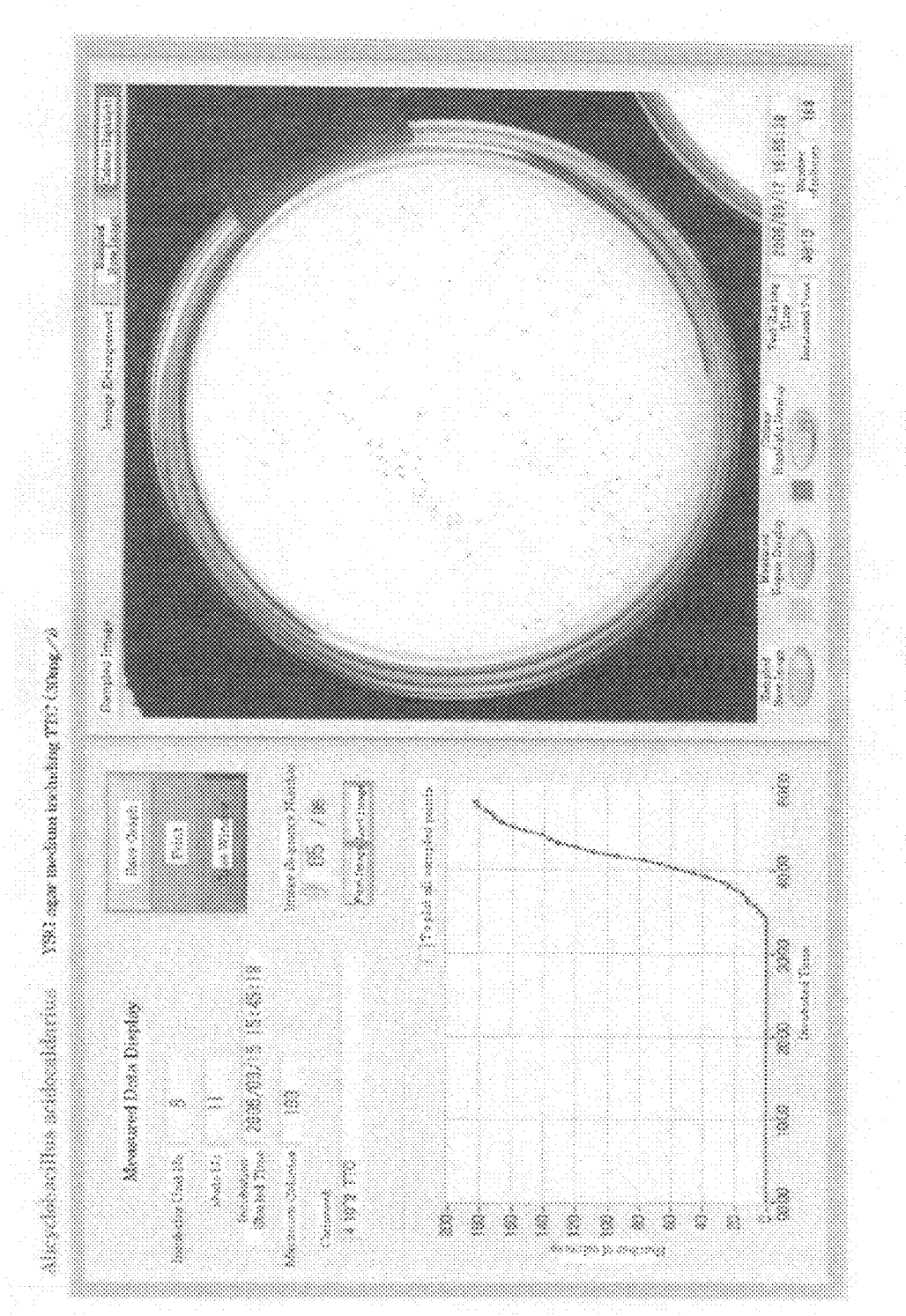
FIG. 3 is a drawing in embodiment representing a graph showing changes in number of colonies depending the culture time when (b) water including *acidocaldarius* is applied to the surface of YSG agar medium including TTC, and a photograph showing colonies on the medium at 48 hours culture.

FIG. 3 represents a graph showing changes in number of colonies depending the culture time when (b) water including *acidocaldarius* is applied to the surface of YSG agar medium including TTC, and a photograph showing colonies on the medium at 48 hours culture. Colonies are shown in red.

Figure 4:
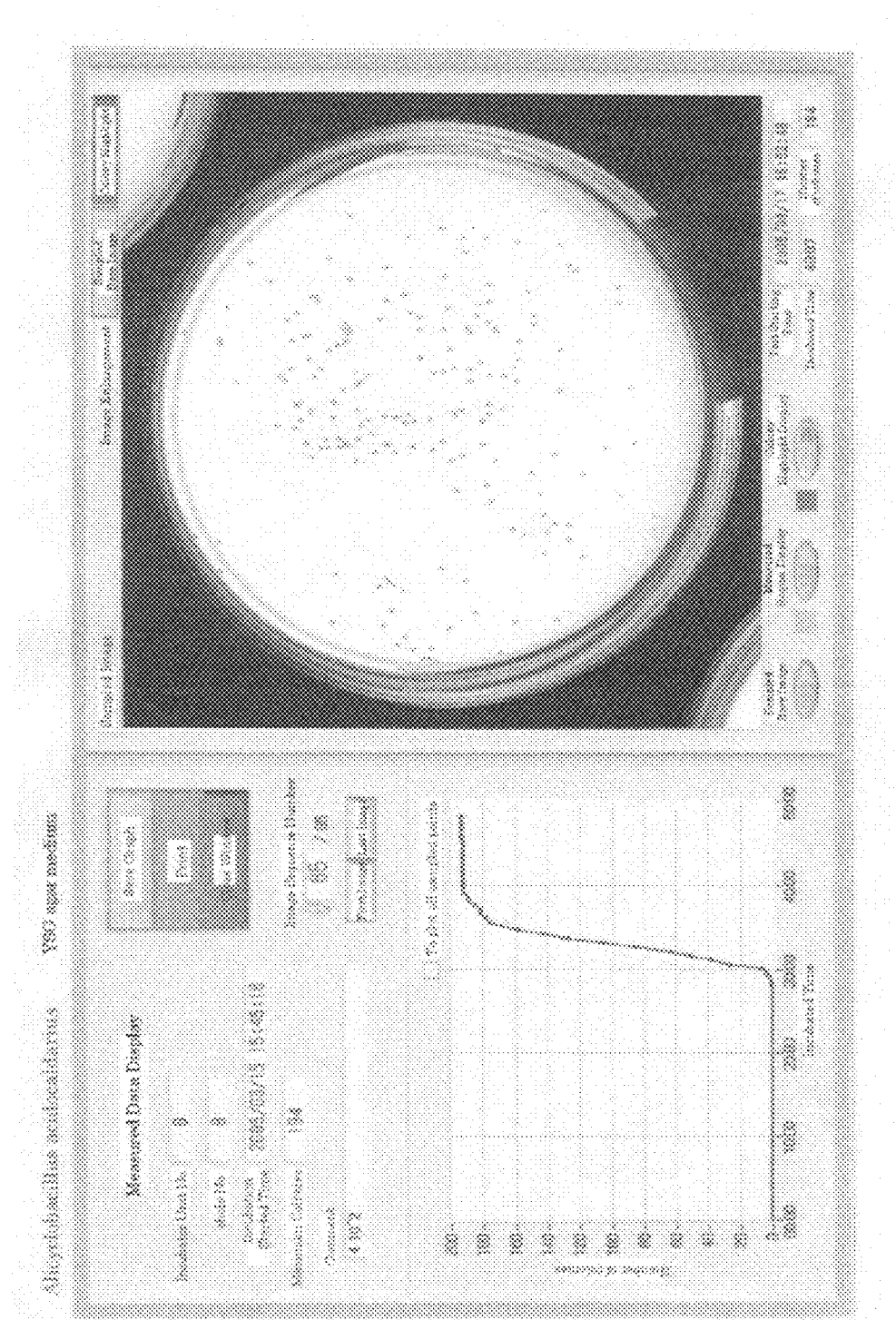
FIG. 4 is a drawing in embodiment representing a graph showing changes in number of colonies depending the culture time when (b) water including *acidocaldarius* is applied to the surface of blank YSG agar medium without TTC, and a photograph showing colonies on the medium at 48 hours culture.

FIG. 4 represents a graph showing changes in number of colonies depending the culture time when (b) water including *acidocaldarius* is applied to the surface of blank YSG agar medium without TTC, and a photograph showing colonies on the medium at 48 hours culture. Colonies are shown in green.

As shown in photographs of colonies in FIGS. 1 and 2, *acidoterrestris* is changed to red in its color and its detection becomes easy. Also, it is known from graphs in FIGS. 1 and 2 that addition of TTC has no effect on the growth rate of *acidoterrestris*. On the other hand, as shown in photographs of colonies in FIGS. 3 and 4, *acidocaldarius* is not changed in its color. Also, it is known from graphs in FIGS. 1 and 2 that addition of TTC has an effect on the growth rate of *acidocaldarius* and the time to detect is delayed longer than 45 hours compared to around 35 hours in the absence of TTC.

What is claimed is:

1. A method for distinguishing a presence of *Alicyclobacilus acidoterrestris* from a presence of *Alicyclobacilus acidocaldarius* in a medium, the method comprising:
   isolating *Alicyclobacilus* bacteria in a sample;
   adding the sample to the medium comprising chlor-2,3,5-triphenyl-2H-tetrazolium (TTC); and
   detecting the presence of *Alicyclobacilus acidoterrestris* based upon color change of a colony of the *Alicyclobacilus acidoterrestris* and *Alicyclobacilus acidocaldarius* on the medium.

2. The method according to claim 1, wherein the color of the colony of the *Alicyclobacilus acidoterrestris* on the medium changes to red.

3. The method according to claim 2, wherein detecting the presence of *Alicyclobacilus acidoterrestris* based upon color change of the colony of the *Alicyclobacilus acidoterrestris* and *Alicyclobacilus acidocaldarius* on the medium comprises:
   correlating the change in color on the medium to red with the presence of *Alicyclobacilus acidoterrestris*.

4. A method for distinguishing a presence of *Alicyclobacilus acidoterrestris* from a presence of *Alicyclobacilus acidocaldarius* in a medium, the method comprising:
   isolating *Alicyclobacilus* bacteria in a sample containing fruit juice;
   adding the sample containing fruit juice to the medium comprising chlor-2,3,5-triphenyl-2H-tetrazolium (TTC); and
   detecting the presence of *Alicyclobacilus acidoterrestris* based upon a colony of the *Alicyclobacilus acidoterrestris* on the medium becoming red.

5. The method according to claim 4, wherein detecting the presence of *Alicyclobacilus acidoterrestris* based upon the colony of the *Alicyclobacilus acidoterrestris* on the medium becoming red comprises:
   correlating the colony becoming red with the presence of *Alicyclobacilus acidoterrestris*.

* * * * *